United States Patent [19]

Takeuchi et al.

[11] Patent Number: 5,693,772
[45] Date of Patent: Dec. 2, 1997

[54] DESALANINEBENANOMICIN A DERIVATIVES AND PROCESSES FOR THE PREPARATION THEREOF

[75] Inventors: Tomio Takeuchi; Shinichi Kondo; Daishiro Ikeda; Toshio Nishizuka, all of Tokyo, Japan

[73] Assignee: Zaidan Hojin Biseibutsu Kagaku Kenkyu Kai, Tokyo, Japan

[21] Appl. No.: 492,007

[22] PCT Filed: Jan. 22, 1993

[86] PCT No.: PCT/JP93/00082

§ 371 Date: Aug. 15, 1995

§ 102(e) Date: Aug. 15, 1995

[87] PCT Pub. No.: WO94/17085

PCT Pub. Date: Aug. 4, 1994

[51] Int. Cl.⁶ .................................................. C07H 1/00
[52] U.S. Cl. ........................... 536/18.5; 536/6.4; 536/18.1
[58] Field of Search ................................ 536/6.4, 18.5, 536/18.1

[56] References Cited

U.S. PATENT DOCUMENTS

| | | | |
|---|---|---|---|
| 4,973,673 | 11/1990 | Sanada et al. | 536/6.4 |
| 5,055,453 | 10/1991 | Takeuchi et al. | 514/27 |
| 5,414,073 | 5/1995 | Okuyama et al. | 536/18.5 |

Primary Examiner—Elli Peselev
Attorney, Agent, or Firm—Larson & Taylor

[57] ABSTRACT

Desalaninebenanomicin A has been synthesized by chemical conversion of benanomicin A. Amino acid derivatives of desalaninebenanomicin A having the general formula (Ia):

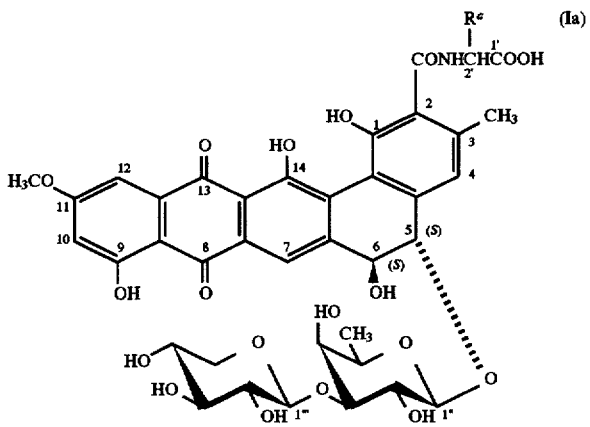

where $R^a$ represents a hyhrogen atom, a $C_{1-5}$ alkyl group, a $C_{1-5}$ hydroxyalkyl group, carboxyl group or a lower alkoxycarbonyl group have been synthesized by condensing the 2-carboxyl group of desalaninebenanomicin A with a variety of amino acids. Among the derivatives of the formula (Ia) having antifungal activities, such desalaninebenanomicin A derivatives in which $R^a$ is a $C_{2-5}$ alkyl group, a $C_{2-5}$ hydroxyalkyl group, carboxyl group or a lower alkoxycarbonyl group are novel semi-synthetic antibiotics having antifungal activities.

3 Claims, No Drawings

1

DESALANINEBENANOMICIN A DERIVATIVES AND PROCESSES FOR THE PREPARATION THEREOF

TECHNICAL FIELD

This invention relates to desalaninebenanomicin A derivatives which are novel antifungal antibiotics, and it also relates to processes for synthesizing the same. This invention is further concerned with desalaninebenanomicin A which is an intermediate for the synthesis of the desalaninebenanomicin A derivatives, and it also relates to a process for preparing desalaninebenanomicin A. Furthermore, this invention embraces a process for the preparation of benanomicin A from desalaninebenanomicin A.

BACKGROUND ART

As such compounds similar in their structure to the desalaninebenanomicin A derivatives which are the novel antifungal antibiotics of this invention, there are benanomicin A which is produced by an actinomycetes, *Actinomadura spadix* MH193-16F4 strain discovered by the present inventors, and benanomicin A-related compounds [see Takeuchi et al., "Journal of Antibiotics" Vol. 41, page 807(1988), U.S. Pat. No. 5,055,453, European Patent Application Publication No. 0315147, Japanese Patent Application Publications (Kokai) Nos. HEI 1-121293, HEI 1-168694, HEI 3-187391 and HEI 2-96317], as well as pradimicin-series antibiotics which are produced by *Actinomadura hibisca* ATCC 53557 strain and reported by Oki et al. [Oki et al., "J. Antibiotics", Vol. 41, page 1701(1988), Sawada et al., "J. Antibiotics", Vol. 43, page 1367(1990)].

These known antibiotics are all characterized by that their chemical structure has a sugar moiety at the 5-position of a benzo[a]naphthacenequinone skeleton and has an amino acid as bonded to the 2-carboxyl group by amido-linkage. In these known antibiotics which have the above chemical structure and are known as the products of the actinomycetes, said amino acid moiety as bonded to the 2-carboxyl group is limited to glycine, alanine and serine. There is no precedent trying to make chemical synthesis of such derivatives of said antibiotics wherein the amino acid moiety has been chemically converted into another amide acid residue.

Through a detailed study by the present inventors, it has been ascertained that, among these antibiotics of benanomicin and pradimicin-series, benanomicin A which has a neutral β-D-xylosyl-β-D-fucosyloxy group as the sugar moiety at the 5-position and has D-alanine as the amino acid at the 2-position [see Japanese Patent Application Publication (Kokai) No. HEI 1-121293, U.S. Pat. No. 5,055,453 and European Patent Application Publication No. 0315147] can exhibit excellent antifungal activities and antiviral activities and also has a low toxicity and a high solubility in water, as compared with the other similar antibiotics. Thus, tests for estimating the safety of benanomicin A are now made with intention to develop it as pharmaceutical drug. Novel semi-synthetic antibiotics are therefore now expected to be produced newly by chemical conversion of benanomicin A.

In the past, a variety of antifungal antibiotics and chemically synthetic antifungal agents have heretofore been studied, but there is only a few of the antifungal agent which have a low toxicity but can exhibit a high antifungal effect. Accordingly, there has been a continued demand for providing novel antifungal agents useful in the field of therapeutic treatment of various infectious diseases caused by fungi.

DISCLOSURE OF THE INVENTION

An object of this invention is to provide new antibiotics having high antifungal activities by a process in which an antibiotic of benanomicin and pradimicin-series is modified by chemically changing the amino acid as bonded to the 2-carboxyl group of the latter antibiotic. In this invention, there are provided novel desalanine-benanomicin A derivatives in which the amino acid as bonded to the 2-carboxyl group of benanomicin A has been converted into threonine, allothreonine, butyrine or aminomalonic acid; as well as processes for the preparation of the same. When the amino acid moiety present in said novel desalaninebenanomicin A derivatives can exist as its D-isomer or L-isomer, the D-isomer is preferred for its capability to afford a higher antifungal activities. This invention also embraces a process for the synthesis of not only such novel derivatives where the amino acid as bonded to the 2-carboxyl group of benanomicin A has been converted into an amino acid of the above-described type such as threonine, but also such known amino acid derivatives of desalaninebenanomicin A where the amino acid moiety is glycine, alanine or serine. This invention further encompasses a process for the synthesis of benanomicin A itself.

In order to achieve the above-mentioned objects, the present inventors have made investigations and had prospected that desalaninebenanomicin A having the following formula (II):

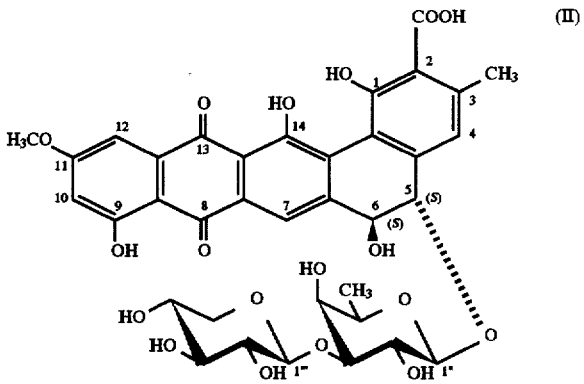

might be prepared by a method wherein as a starting material is used benanomicin A which corresponds to a compound of the formula (I) given hereinafter (where R is methyl group and its stereochemistry is (2'R)) and which is represented by the formula (A):

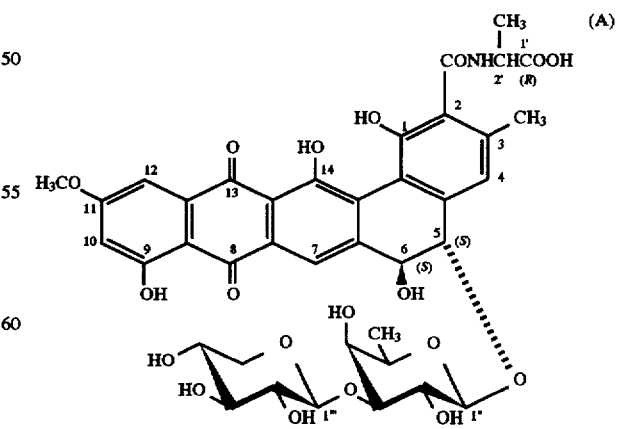

and is available by cultivation of actinomycetes, *Actinomadura spadix* MH193-16F4 strain (FERM BP-9529) as disclosed in the Japanese Patent Application Publication (Kokai) No. HEI 1-121293 or U.S. Pat. No. 5,055,453 and wherein the alanine moiety, that is, the amino acid as bonded by amido-linkage to the 2-carboxyl group of benanomicin A, is removed therefrom. The present inventors also had presumed that various amino acid derivatives could be synthesized from such prospective desalaninebenanomicin A by bonding different amino acids to its 2-carboxyl group by amido-linkage. Although we, the present inventors, had tried to effect immediately a reaction for cleaving the amido-linkage of benanomicin A by hydrolyzing benanomicin A under conventional conditions for hydrolysis, we could not obtain any satisfactory results which achieved the synthesis of desalaninebenanomicin A as intended.

As a result of further investigation, we, the present inventors, have now found that such a protected iminoether derivative of benanomicin A which is represented by the formula (B):

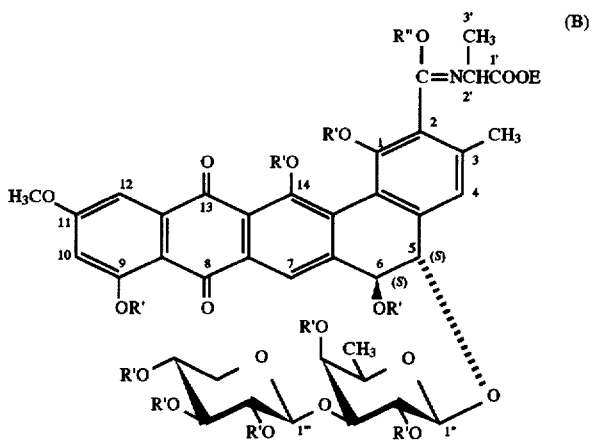

where E represents an ester-forming group, R' represents a hydroxyl-protecting group and R" represents a lower alkyl group which will be determined depending on the kind of a Meerwein reagent employed, is possible to be prepared by such a process wherein the terminal carboxyl group of the side chain at the 2-position of benanomicin A is protected with the ester-forming group which may be an ordinary carboxyl-protecting group, such as a lower alkyl group, e.g., methyl and ethyl, or diphenylmethyl group or methoxybenzyl group, and the resulting benanomicin A ester is then subjected to the reaction for protection of its nine hydroxyl groups each with an ordinary hydroxyl-protecting group such as acetyl, followed by being subjected to a known reaction for iminoetherification using a Meerwein reagent, or a phosphorus pentachloride/pyridine reagent or the like so that the amido-linkage of benanomicin A is changed into iminoether.

When both the hydroxyl-protecting groups and carboxyl-protecting group are then removed from the compound of the above formula (B), it is possible to produce an iminoether compound having the following formula (C):

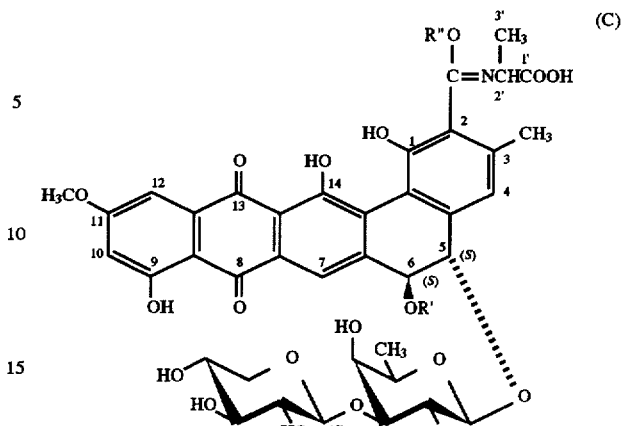

where R" has the same meaning as defined above. We, the present inventors, have found that when the resultant compound of the formula (C) is subjected to a reaction for cleaving the iminoether-bond of the compound (C), for example, by heating the compound (C) in a mixed solution of acetone and water, under refluxing, there can successfully be synthetized an ester of the aimed desalaninebenanomicin A of the formula (II). This ester may be converted by usual alkaline hydrolysis into desalaninebenanomicin A of the formula (II) in the form of free acid or in the form of a salt.

Furthermore, we, the present inventors, have now succeeded in synthesizing a desalaninebenanomicin A derivative having the following general formula (Ia):

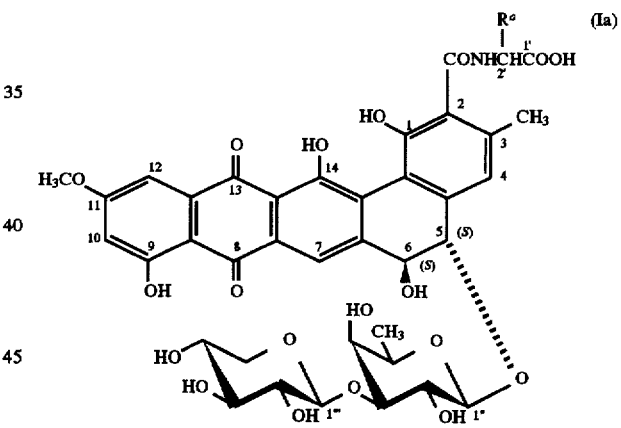

where $R^a$ represents a hydrogen atom, a $C_{1-5}$ alkyl group, a $C_{1-5}$ hydroxyalkyl group, carboxyl group or a lower alkoxycarbonyl group, by conducting such a process wherein the nine hydroxyl groups of desalaninebenanomicin A of the formula (II) are each protected with an ordinary hydroxyl-protecting group such as a lower alkanoyl group, e.g., acetyl or an aroyl group, e.g., benzoyl, and wherein the resulting protected derivative is then condensed with an amino acid ester of the formula (III):

where $R^a$ represents a hydrogen atom, a $C_{1-5}$ alkyl group, $C_{1-5}$ hydroxyalkyl group, carboxyl group or a lower alkoxycarbonyl group and R' represents a lower alkyl group, in accordance with a known reaction for formation of an amide, followed by removing both the hydroxyl-protecting groups and carboxyl-protecting group from the resulting condensation product.

Among the desalaninebenanomicin A derivatives of the general formula (Ia), such those which are containing a hydrogen atom, methyl group or hydroxymethyl group as $R^a$ are known compounds.

Among the derivatives of the general formula (Ia), on the other hand, such those which are containing a $C_{2-5}$ alkyl group, a $C_{2-5}$ hydroxyalkyl group, carboxyl group or a lower ($C_{1-6}$) alkoxy-carbonyl group as $R^a$ are novel compounds such that the present inventors have found these novel compounds to have antifungal activities. On the basis of the above-described various findings, the present invention has been completed.

In a first aspect of the present invention, therefore, there is provided a novel antifungal antibiotic, namely a desalaninebenanomicin A derivative represented by the following general formula (I):

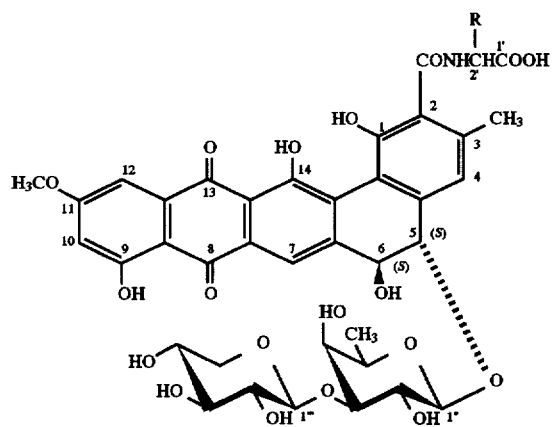

wherein R represents a $C_{2-5}$ alkyl group or a $C_{2-5}$ hydroxyalkyl group, carboxyl group or a lower alkoxycarbonyl group, or a salt thereof.

The derivative of the general formula (I) includes D-threonine, D-allothreonine, D-butyrine and aminomalonic acid derivatives which will be described below, respectively.

BEST MODES FOR CARRYING OUT THE INVENTION

[A] physicochemical Properties

1. Physicochemical properties of the D-threonine derivative [the compound of the general formula (I) where R is —CH(OH)CH$_3$ and the stereochemistry is (2'R,3'S)]
 (1) Color and appearance: Red powder
 (2) Molecular formula: $C_{40}H_{43}NO_{20}$
 (3) Mass spectrum (FABMS): m/z 857 (M$^-$)
 (4) Melting point: >220° C. (decomposed)
 (5) Ultraviolet and visible-ray absorption spectrum ($\lambda_{max}$, nm): 230, 288, 305, 465.
 (6) Infrared absorption spectrum (KBr, cm$^{-1}$): 3400, 2920, 1726, 1628, 1608, 1447, 1431, 1377, 1334, 1298, 1256, 1236, 1209, 1163, 1076, 1045, 997, 970.
 (7) $^1$H-NMR spectrum (400 MHz, DMSO-d$_6$): 12.80(1H), 8.09(1H), 7.73(1H), 7.30(1H), 7.22(1H), 6.92(1H), 4.63 (1H), 4.60(1H), 4.53(1H), 4.42(2H), 4.18(1H), 3.95(3H), 3.71(2H), 3.55(2H), 3.30(1H), 3.1(3H), 2.35(3H), 1.20(3H), 1.14(3H).
 (8) $^{13}$C-NMR spectrum (100 MHz, DMSO-d$_6$): 187.4, 184.9, 171.7, 167.2, 165.9, 164.6, 156.8, 151.0, 147.8, 138.1, 137.3, 134.3, 131.3, 127.3, 125.5, 115.5, 113.7, 110.0, 107.5, 106.8, 105.1, 104.3, 82.9, 75.9, 73.5, 70.3, 70.0, 69.3, 66.4, 65.5, 57.9, 56.3, 20.2, 19.2, 16.2.

This D-threonine derivative described above is a novel compound which can be named as (2'R,3'S)-3'-hydroxy-3'-methylbenanomicin A., 2. Physicochemical properties of the D-allothreonine derivative [the compound of the general formula (I) where R is —CH(OH)CH$_3$ and the stereochemistry is (2'R,3'R)]
 (1) Color and appearance: Red powder
 (2) Molecular formula: $C_{40}H_{43}NO_{20}$
 (3) Mass spectrum (FABMS): m/z 857 (M$^-$)
 (4) Melting point: >223° C. (decomposed)
 (5) Ultraviolet and visible-ray absorption spectrum ($\lambda_{max}$, nm): 235, 288, 310, 460
 (6) Infrared absorption spectrum (KBr, cm$^{-1}$): 3450, 1734, 1645, 1448, 1394, 1334, 1298, 1257, 1236, 1209, 1165, 1076, 999, 970.
 (7) $^1$H-NMR spectrum (270 MHz, DMSO-d$_6$): 12.80(1H), 8.17(1H), 8.09(1H), 7.31(1H), 7.21(1H), 6.93(1H), 4.62 (1H), 4.58(1H), 4.53(1H), 4.42(2H), 3.96(4H), 3.73(2H), 3.62(3H), 3.30(1H), 3.1(3H), 2.31(3H), 1.20(3H), 1.13(3H).
 (8) $^{13}$C-NMR spectrum (67.5 MHz, DMSO-d$_6$): 186.4, 185.2, 171.6, 167.2, 166.3, 164.5, 158.0, 152.0, 147.2, 138.0, 137.2, 134.8, 131.3, 127.1, 126.5, 115.9, 114.3, 110.0, 107.2, 106.4, 105.1, 104.4, 82.9, 75.9, 73.5, 70.3, 70.0, 69.3, 66.6, 65.5, 58.6, 56.2, 19.9, 19.3, 16.2.

This D-allothreonine derivative described above is a novel compound which can be named as (2'R,3'R)-3'-hydroxy-3'-methylbenanomicin A.

3. Physicochemical properties of the D-butyrine derivative [the compound of the general formula (I) where R is —CH$_2$CH$_3$ and the stereochemistry is (2'R)]
 (1) Color and appearance: Red powder
 (2) Molecular formula: $C_{40}H_{43}NO_{19}$
 (3) Mass spectrum (FABMS): m/z 841 (M$^-$)
 (4) Melting point: 228°–234° C. (decomposed)
 (5) Ultraviolet and visible-ray absorption spectrum ($\lambda_{max}$, nm): 270, 295, 490.
 (6): Infrared absorption spectrum (KBr, cm$^{-1}$): 3415 1734, 1626, 1446, 1385, 1334, 1296, 1259, 1209, 1165, 1074, 1045, 999, 968.
 (7) $^1$H-NMR spectrum (270 MHz, DMSO-d$_6$): 12.8(1H), 8.30(1H), 8.10(1H), 7.32(1H), 7.22(1H), 6.93(1H), 1.13 (3H), 0.97(3H).
 (8) $^{13}$C-NMR spectrum (67.5 MHz, DMSO-d$_6$): 188.0, 185.5, 173.8, 167.7, 166.5, 165.2, 157.3, 156.5, 151.5, 138.4, 137.8, 134.9, 131.8, 127.7, 126.1, 119.2, 116.1, 114.1, 110.6, 108.1, 107.4, 105.7, 76.5, 74.0, 72.4, 71.5, 70.8, 70.6, 69.9, 66.1, 56.9, 54.0, 24.6, 19.6, 16.8, 10.9.

This D-butyrine derivative described above is a novel compound which can be named as (2'R)-3'-methylbenanomicin A.

4. Physicochemical properties of the aminomalonic acid derivative [the compound of the general formula (I) where R is —COOH]
 (1) Color and appearance: Red powder
 (2) Molecular formula: $C_{39}H_{37}NO_{21}Na_2$
 (3) Mass spectrum (FABMS): m/z 901 (M$^{-1}$)
 (4) Melting point: 216°–218° C. (decomposed)
 (5) Ultraviolet and visible-ray absorption spectrum ($\lambda_{max}$, nm): 240, 274, 323, 498.
 (6) Infrared absorption spectrum (KBr, cm$^{-1}$): 3400, 1618, 1491, 1442, 1385, 1332, 1296, 1260, 1163, 1074, 1044, 995, 966.
 (7) $^1$H-NMR spectrum (270 MHz, D$_2$O): 8.05(1H), 7.66 (1H), 7.45(1H), 7.05(1H), 5.23(1H), 5.19(1H), 5.14(1H), 5.03(1H), 4.99(1H), 4.3(4H), 4.21(1H), 4.15(1H), 4.1–3.9 (3H), 3.83(1H), 3.71(1H), 3.67(1H), 2.63(3H), 1.55(3H).
 (8) $^{13}$C-NMR spectrum (67.5 MHz, D$_2$O-d$_6$): 188.2, 184.6, 175.4, 172.0, 165.1, 156.0, 144.1, 140.9, 138.2, 137.4, 130.4, 129.8, 122.9, 122.0, 120.5, 116.5, 115.8, 111.5, 105.7, 104.6, 103.9, 83.7, 81.4, 77.1, 74.7, 72.5, 72.1, 71.4, 70.7, 66.5, 56.8, 19.5, 16.6.

This aminomalonic acid derivative described above is a novel compound which can be named as 2'-carboxy-2'-demethylbenanomicin A.

[B] Biological Activities

Antifungal activities of the novel desalaninebenanomicin A derivatives of the formula (I) according to the present invention against a variety of fungi were determined by the serial dilution method on a nutrient agar medium containing 1% glucose (incubated at 27° C. for 42 hours). Their minimum inhibitory concentrations (μg/ml) as measured above are shown in Table 1 below.

TABLE 1

| Microorganisms tested | The derivatives of the general formula (I) according to this invention | | | |
|---|---|---|---|---|
| | D-threonine derivative | D-allo-threonine derivative | D-butyrine derivative | Amino-malonic acid derivative |
| Candida tropicalis F-1 | 25 | 12.5 | 12.5 | 25 |
| Candida pseudotropicalis F-2 | 6.25 | 6.25 | 3.13 | 6.25 |
| Candida albicans 3147 | 25 | 12.5 | 12.5 | 25 |
| Candida sp. Yu1200 | 12.5 | 12.5 | 12.5 | 25 |
| Candida krusei F-5 | 12.5 | 12.5 | 12.5 | 25 |
| Saccharomyces cerevisiae F-7 | 12.5 | 6.25 | 3.13 | 6.25 |
| Cryptococcus neoformans F-10 | 12.5 | 6.25 | 6.25 | 25 |
| Cochliobolus miyabeanus | >100 | >100 | >100 | >100 |
| Pyricularia oryzae | >100 | >100 | 100 | >100 |
| Pellicularia sasakii | >100 | 12.5 | 12.5 | 12.5 |
| Aspergillus niger F-16 | >100 | >100 | 100 | >100 |
| Aspergillus fumigatus F-181 | 100 | 50 | 50 | >100 |
| Trichophyton asteroides 429 | >100 | >100 | >100 | >100 |
| Trichophyton mentagrophytes F-15 | >100 | >100 | >100 | >100 |

In a second aspect of the present invention, there is provided a process for the preparation of a desalaninebenanomicin A derivative of the general formula (Ia) where $R^a$ represents a hydrogen atom, a $C_{1-5}$ alkyl group or a $C_{1-5}$ hydroxyalkyl group, carboxyl group or a lower alkoxycarbonyl group, which comprises chemically converting an antibiotic, benanomicin A, into desalaninebenanomicin A of the formula (II) and then producing, by a chemical derivation from the resulting antifungal antibiotic compound of the formula (II), the desalaninebenanomicin A derivative of the general formula (Ia) above.

The process according to the second aspect of the present invention embraces such a process for the preparation of a desalaninebenanomicin A derivative of the general formula (Ia), which process comprises protecting the nine hydroxyl groups of desalaninebenanomicin A of the formula (II) each with an ordinary hydroxyl-protecting group such as a lower alkanoyl group, e.g., acetyl, or an aroyl group, e.g., benzoyl, condensing the resulting hydroxyl-protected derivative with an amino acid ester of the following formula (III):

where $R^a$ represents a hydrogen atom, a $C_{1-5}$ alkyl group or a $C_{1-5}$ hydroxyalkyl group, carboxyl group or a lower alkoxycarbonyl group and R' represents a lower alkyl group, by a known reaction for formation of an amide, and removing the hydroxyl-protecting groups and carboxyl-protecting group from the resulting condensation product.

In the above-mentioned process, the ordinary hydroxyl-protecting groups may be employed for the protection of the hydroxyl groups of desalaninebenanomicin A. Desirable are such hydroxyl-protecting groups which can be removed easily and also can be eliminated simultaneously with the removal of the carboxyl-protecting group and which may preferably be, for example, protective acetyl group removable by alkaline hydrolysis. The reaction for formation of amide may be carried out in a known manner using the azide method, the acid chloride method, the acid anhydride method, the active ester method or the like. Particularly preferred is the active ester method which makes use of N-hydroxysuccinimide, 1-hydroxybenzotriazole or the like.

To recover the target desalaninebenanomicin A derivative of the general formula (Ia) from the reaction solution as resulted from the reaction for the amide-formation, there may be conducted conventional purification methods, which can utilize the properties of the derivative (Ia) suitably, for instance, the solvent-extracting method, the ion-exchange resin method, the adsorptive or partition chromatographic method, the gel filtration method, the dialysis method and the precipitation method, either singly or in combination, as the case demands.

The desalaninebenanomicin A derivative of the general formula (Ia) so obtained may be separated in its free acid form. Alternatively, a solution containing the desalaninebenanomicin A derivative or its concentrated solution may be treated, upon operation of each of the purification steps, with a base, including an inorganic base such as an alkali metal compound, e.g., sodium hydroxide or potassium hydroxide, an alkaline earth metal compound, e.g., calcium hydroxide or magnesium hydroxide or an ammonium salt, or an organic base, e.g., ethanolamine, triethylamine or dicyclohexylamine, so that the desalaninebenanomicin A derivative can be converted into its corresponding salt and separated in the salt form.

Besides, the salt of the desalaninebenanomicin A derivative of the general formula (Ia), which has been prepared as described above, may be converted into the free acid form, namely the desalaninebenanomicin A itself, in a manner known per se in the art. The desalaninebenanomicin A derivative as obtained in the free acid form may then be converted into its corresponding salt by treating with a base exemplified above, in a known manner. Accordingly, not only the desalaninebenanomicin A derivatives of the general formula (Ia) and of the general formula (I) but also their salts as illustrated above should be embraced within the scope of the present invention.

In a third aspect of the present invention, there are provided desalaninebenanomicin A having the following formula (II):

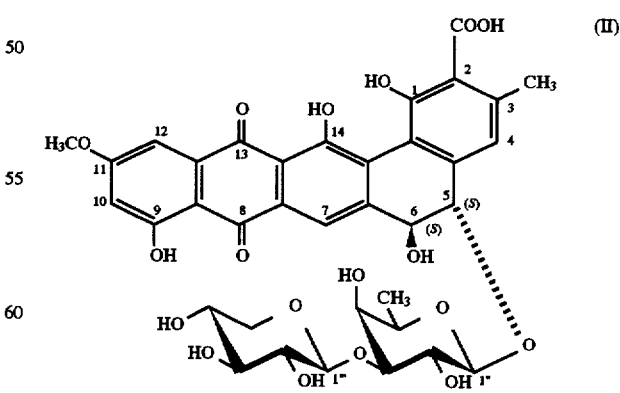

and, salts and esters thereof, particularly including the alkyl esters. These compounds are useful as intermediates for the synthesis of the antifungal desalaninebenanomicin A derivatives in accordance with the present invention.

1. Physicochemical properties of desalaninebenanomicin A (1) Color and appearance: Red powder (2) Molecular formula: $C_{36}H_{36}O_{18}$ (3) Mass spectrum (FABMS): m/z 756 (M⁻)

(4) Melting point: >220° C. (decomposed)

(5) Ultraviolet and visible-ray absorption spectrum (MeOH, $\lambda_{max}$, nm): 207, 238, 285, 455.

(6) Infrared absorption spectrum (KBr, $cm^{-1}$): 3422, 2984, 2930, 1746, 1608, 1447, 1385, 1334, 1259, 1163, 1074, 1045, 999, 968.

(7) ¹H-NMR spectrum (400 MHz, DMSO-$d_6$, δ ppm): 12.83(1H), 8.00(1H), 7.26(1H), 7.18(1H), 6.91(1H), 6.12 (1H), 4.62(2H), 4.51(1H), 4.40(1H), 3.93(3H), 3.68(2H), 3.58(2H), 3.52(1H), 3.27(1H), 3.08(4H), 2.45(3H), 1.10 (3H).

(8) ¹³C-NMR spectrum (100 MHz, DMSO-$d_6$, δ ppm): 187.0, 185.1, 171.1, 165.9, 164.6, 157.6, 155.5, 147.4, 140.6, 139.4, 134.5, 131.4, 125.3, 118.2(x2), 115.4, 114.8, 114.2, 110.0, 107.3, 106.6, 105.0, 104.2, 82.8, 81.3, 75.9, 73.5, 71.6, 70.3, 70.0, 69.9, 69.3, 65.5, 56.2, 21.5, 16.2

2. Physicochemical properties of desalaninebenanomicin A methyl ester (1) Color and appearance: Red powder (2) Molecular formula: $C_{37}H_{38}O_{18}$ (3) Mass spectrum (FABMS): m/z 770 (M⁻)

(4) Melting point: 199°–206° C. (decomposed)

(5) Ultraviolet and visible-ray absorption spectrum ($\lambda_{max}$, nm): 235, 285, 470.

(6) Infrared absorption spectrum (KBr, $cm^{-1}$): 3425, 1720, 1624, 1447, 1387, 1260, 1163, 1070.

(7) ¹H-NMR spectrum (400 MGz, DMSO-$d_6$, δ ppm): 12.80(1H), 8.00(1H), 7.26(1H), 7.17(1H), 6.90(1H), 6.07 (1H), 5.68(1H), 5.0(3H), 4.62(3H), 4.49(2H), 4.40(1H), 3.94(3H), 3.82(3H), 3.69(2H), 3.60(2H), 3.52(1H), 3.3(1H), 3.08(4H), 2.25(3H), 1.10(3H).

(8) ¹³C-NMR spectrum (100 MHz, DMSO-$d_6$, δ ppm): 186.5, 185.4, 168.8, 166.0, 164.4, 147.1, 139.3, 134.6, 131.7, 123.0, 115.9, 114.5, 110.1, 107.4, 106.5, 105.4, 83.1, 76.1, 73.7, 71.8, 70.4, 70.1, 69.4, 65.7, 56.4, 52.0, 19.7, 16.4.

In the fourth aspect of the invention, there is also provided a process for the preparation of desalaninebenanomicin A of the formula (II) useful as an intermediate, which process comprises chemically converting the antibiotic benanomicin A into desalaninebenanomicin A of the formula (II).

One embodiment of the process according to the fourth aspect of the present invention embraces such a process for the synthesis of an ester of desalaninebenanomicin A of the formula (II) wherein the carboxyl group of benanomicin A having the formula (A) is protected with a conventional ester-forming group such as methyl, ethyl, methoxybenzyl or diphenylmethyl group, followed by protecting the nine hydroxyl groups of benanomicin A each with a usual hydroxyl-protecting group such as acetyl group, and the resulting protected derivative of benanomicin A is then subjected to a known reaction for imino-etherification with using the Meerwein reagent or phosphorus pentachloride/pyridine reagent, thereby to convert the amido-bond of benanomicin A into the corresponding iminoether and to produce a protected iminoether derivative having the formula (IV):

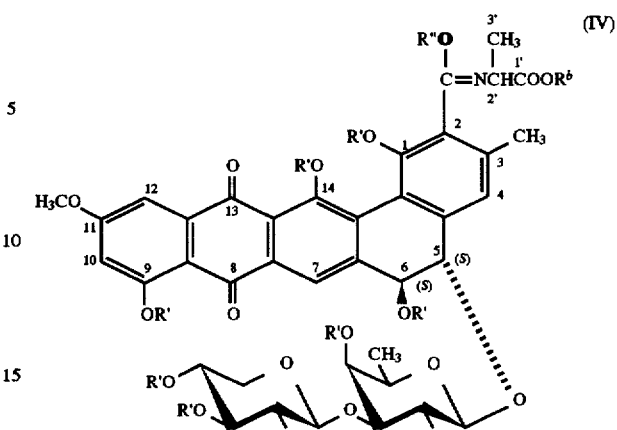

where $R^b$ represents an ester-forming group, R' represents a hydroxyl-protecting group and R" represents a lower alkyl group which is determined by the Meerwein reagent employed, and wherein the hydroxyl-protecting groups and carboxyl-protecting group are then removed from the iminoether derivative of the formula (IV) to produce a compound of the formula (C), and the resultant compound (C) is subjected to a reaction for cleaving the iminoether linkage of the compound (C). The ester of desalaninebenanomicin A so obtained may be converted, by conventional alkaline hydrolysis, into desalaninebenanomicin A of the formula (II) in the form of free acid or in the form of a salt.

Examples of the Meerwein reagent usable in the above mentioned process for effecting the reaction of imino-etherification may include a trialkyloxonium tetrafluoroborate containing lower alkyl groups such as methyl and/or ethyl groups. The alkyl group [namely, R" present in the formula (IV)] of the resulting iminoether compound will be determined depending on the alkyl groups present in the Meerwein reagent employed. The reaction for cleaving the iminoether linkage of the compound of the formula (IV) may preferably be conducted after effecting the removal of the protective groups from the compound (IV). The reaction for cleaving the iminoether linkage may be conducted in an aqueous organic solvent such as aqueous acetone or aqueous methanol by heating the solution under reflux. In order to perform the procedure that the target desalaninebenanomicin A of the formula (II) in the form of a free acid or an ester is recovered from the resultant reaction solution, it is possible to make a general purification method, which makes use of the properties of the target final product suitably, for instance, solvent extraction method, ion-exchange resin method, adsorptive or partition chromatographic, method, gel filtration method, dialysis method and precipitation method, either singly or in combination, as the case demands.

Desalaninebenanomicin A of the formula (II) so obtained may be separated in the form of its free acid. Alternatively, a solution containing desalaninebenanomicin A or its concentrated solution may be treated, upon operation of each step for the purification, with a base, inclusive of an inorganic base such as an alkali metal compound, e.g., sodium hydroxide or potassium hydroxide, an alkaline earth metal compound, e.g., calcium hydroxide or magnesium hydroxide, or an ammonium salt, or an organic base such as ethanolamine, triethylamine or dicyclohexylamine, so that desalaninebenanomicin A can be converted into and separated in the form of the corresponding salt.

Besides, the salt so prepared of desalaninebenanomicin A of the formula (II) may be converted into the free acid form, namely as desalaninebenanomicin A itself, in a manner known per se in the art. The desalaninebenanomicin A as obtained in the free acid form may be converted into its corresponding salt by treating in a known manner with a base as exemplified above. Accordingly, desalanienbenanomicin A as well as its salts as illustrated above should be embraced within the scope of the present invention. Further, when desalaninebenanomicin A is reacted with a lower alkanol such as methanol or ethanol, the carboxyl group of desalaninebenanomicin A is converted into its corresponding lower alkyl ester.

The present invention will hereinafter be illustrated by Examples. As the properties of desalaninebenanomicin A and its derivatives have been elucidated by this invention, it is feasible to devise various processes for the preparation of desalaninebenanomicin A and its amido derivatives with utilizing the properties of desalaninebenanomicin A and its derivatives.

This invention is thus limited in no way to the Examples, but it embraces not only any modification of the procedures of the following Examples, but also all such processes wherein desalaninebenanomicin A and its amido derivatives are prepared, extracted and purified in a manner known per se in the art with utilization of the properties of desalaninebenanomicin A and its amino acid derivatives.

EXAMPLE 1

Production of the methyl ester of desalaninebenanomicin A (a) Preparation of the diphenylmethyl ester of benanomicin A In a mixed solution of 50 ml of dimethylformamide (DMF) and 50 ml of methanol were suspended 3.0 g of benanomicin A in the form of free acid [U.S. Pat. No. 5,055,453], followed by the addition of 1.1 g of diphenyldiazomethane at room temperature. The resulting mixture was stirred overnight. The resultant reaction solution was concentrated to about half of its initial volume under reduced pressure, followed by the addition of 200 ml of water. The red solid so precipitated was collected by filtration. The red solid was added into a mixed solution of 200 ml of ethyl acetate and 200 ml of water, followed by vigorous stirring for 30 minutes. The insoluble red solid so obtained was collected by filtration and washed with water, whereby 3.02 g of the titled compound were obtained. FABMS: 993(M⁻)

(b) Preparation of the diphenylmethyl ester of nona-O-acetylbenanomicin A

In 120 ml of anhydrous pyridine were dissolved 3.0 g of the diphenylmethyl ester of benanomicin A as obtained in the above procedure, and the resulting solution was added with 60 ml of acetic anhydride. The resulting mixture was stirred at 50° C. for 3 hours. The reaction solution obtained was concentrated under reduced pressure, and the resulting oil was mixed with 100 ml of water to deposit a powdery solid. This solid was collected by filtration and washed repeatedly with water. Thus, 4.12 g of the titled compound, ie., the nona-O-acetyl derivative, were yielded as a yellowish orange solid. FABMS: 1370 (M–1)⁻

(c) Preparation of the methyl ester of desalaninebenanomicin A

In 80 ml of anhydrous dichloromethane was dissolved 4.21 g of the diphenylmethyl ester of nona-O-acetylbenanomicin A, and the resulting solution was added with 2.27 g of trimethyloxonium tetrafluoroborate. The resulting mixture was stirred overnight at room temperature. The reaction solution obtained was added with 100 ml of a saturated aqueous solution of sodium hydrogen carbonate, followed by vigorous stirring for 30 minutes. The resulting mixture was then separated into two phases. The organic solvent phase obtained was washed successively with 5% aqueous citric acid and water and then dried over anhydrous magnesium sulfate. The solvents were distilled off from the dried solution under reduced pressure, whereby 3.99 g of the corresponding nona-O-acetylated iminoether derivative were obtained.

The nona-O-acetylated iminoether derivative as obtained was dissolved in 40 ml of methanol, followed by the addition of 40 ml of a 1M aqueous solution of sodium hydroxide. The resulting mixture was stirred overnight at room temperature. Methanol was distilled off from the resulting reaction solution under reduced pressure. The residue obtained was thereafter adjusted to pH 1.6 with 1M hydrochloric acid under ice-cooling. The orange solid so precipitated was separated by centrifugation. The solid obtained was rinsed with water and dried, whereby the deacetylated iminoether derivative was obtained as a yellowish red powder.

The powder was then dissolved in a mixed solvent of 60 ml of acetone and 30 ml of water, followed by heating at 60° C. under reflux for 3 hours (for the cleavage of the iminoether linkage). Acetone was distilled off from the reaction solution under reduced pressure. The red solid precipitated was separated by centrifugation to afford a red solid. The solid obtained was purified by chromatography on a silica gel column (with developing solvent made of chloroform-butanol-pyridine-water, 4:2:2.5:0.3), whereby 1.36 g of the methyl ester of desalaninebenanomicin A were afforded.

EXAMPLE 2

Production of desalaninebenanomicin A

To 640 mg of the methyl ester of desalaninebenanomicin A obtained in the above Example 1 were added 16 ml of methanol and 64 ml of a 2M aqueous solution of sodium hydroxide. The mixture obtained was stirred at 70° C. for 24 hours. The resulting reaction solution was adjusted to pH 1.6 with 3M hydrochloric acid under ice-cooling, and the solid precipitated was collected by filtration and rinsed with water.

The solid obtained was subjected to chromatography on a silica gel column (with developing solvent made of chloroform-butanol-pyridine-water, 4:3:5:1), whereby a pyridinium salt of desalaninebenanomicin A was obtained as a red solid. This solid was dissolved in 50 ml of water and the resulting solution was adjusted to pH 1.6 with 1M hydrochloric acid. The solid precipitated was separated by centrifugation, whereby 430 mg of desalaninebenanonicin A in the form of the free acid was afforded as an orange solid.

EXAMPLE 3

Preparation of nona-O-acetyl-desalaninebenanomicin A

In 10 ml of anhydrous pyridine was dissolved 640 mg of desalaninebenanomicin A in the free acid form, which had been obtained in the above Example 2. The resulting solution was added with 5 ml of acetic anhydride, followed by stirring at 70° C. for 3 hours. The reaction solution obtained was concentrated under reduced pressure, and the resulting solid was purified by chromatography on a silica gel column (with developing solvent made of chloroform-methanol-water, 50:1:0.05), whereby 643 mg of nona-O-acetyl-desalaninebenanomicin A were yielded.

FABMS: m/z 1134(M⁻).

EXAMPLE 4

Production of (2'S,3'R)-3'-hydroxy-3'-methylbenanomicin A [The L-threonine derivative]

In 4 ml of acetonitrile were dissolved 100 mg of nona-O-acetyl-desalaninebenanomicin A as obtained in the above Example 3, and also 74 mg of 1-hydroxybenzotriazole hydrate. The resulting solution was added with 3 ml of a solution containing 168 mg of para-toluenesulfonate of L-threonine diphenylmethyl ester and 60 µl of N-methylmorpholine in acetonitrile. Dicyclohexylcarbodiimide (57 mg) was added to the resulting mixture under ice-cooling, followed by reaction for one hour and then reaction at room temperature for 3 hours (for the reaction for formation of amide).

The resulting reaction solution was added with 0.2 ml of acetic acid, followed by stirring for one hour. The precipitate as formed was removed by filtration. The filtrate obtained was concentrated under reduced pressure. The resultant residue was dissolved in 20 ml of ethyl acetate, and the solution was washed successively with a 10% aqueous solution of citric acid, a saturated aqueous solution of sodium hydrogen carbonate and water and then dried over anhydrous magnesium sulfate. The solvent was distilled off from the dried solution under reduced pressure, whereby 120 mg of the condensation product were obtained.

The condensation product so obtained (100 mg) was dissolved in a mixture of 5 ml of methanol and 3 ml of pyridine, followed by the addition of 10 ml of a 0.2M aqueous solution of potassium carbonate. The resulting mixture was stirred overnight at 70° C. (for the reactions of deprotection). After ice-cooling, the resulting reaction solution was adjusted to pH 2.0 with 1M hydrochloric acid. The solid precipitated was separated by centrifugation to obtain a red solid. The solid obtained was purified by chromatography on a silica gel column (with developing solvent made of chloroform-butanol-pyridine-water, 4:2:2.5:0.3), whereby a pyridine salt of (2'S,3'R)-3'-hydroxy-3'-methylbenanomicin A was yielded.

The pyridine salt as obtained was dissolved in 20 ml of water, followed by adsorbing on a column of an adsorbent resin, "Diaion HP-20", and then eluting with 70% aqueous acetonitrile. The eluate was concentrated under reduced pressure, and the solid obtained was again suspended in water. The resulting suspension was adjusted to pH 2.0 with 2M hydrochloric acid, and the precipitate deposited was separated by centrifugation, whereby 10 mg of (2'S,3'R)-3'-hydroxy-3'-methylbenanomicin A in the form of the free acid were obtained FABMS: 857(M⁻).

EXAMPLE 5

Production of (2'R,3'S)-3'-hydroxy-3'-methylbenanomicin A [the D-threonine derivative]

In a similar manner to the preparation process as described above in Example 4, 30 mg of (2'R,3'S)-3'-hydroxy-3'-methylbenanomicin A in the form of the free acid were produced from 100 mg of nona-O-acetyl-desalaninebenanomicin A and 168 mg of para-toluenesulfonate of D-threonine diphenylmethyl ester. FABMS: 857(M⁻).

EXAMPLE 6

Preparation of (2'S,3'S)-3'-hydroxy-3'-methylbenanomicin A [the L-allothreonine derivative]

In a similar manner to the preparation process as described above in Example 4, 6.4 mg of (2'S,3'S)-3'-hydroxy-3'-methylbenanomicin A in the form of the free acid were obtained from 100 mg of nona-O-acetyl-desalaninebenanomicin A and 168 mg of para-toluenesulfonate of L-allothreonine diphenylmethyl ester. FABMS: 857(M⁻).

EXAMPLE 7

Preparation of (2'R,3'R)-3'-hydroxy-3'-methylbenanomicin A [the D-allothreonine derivative]

In a similar manner to the preparation process as described above in Example 4, 1.5 mg of (2'R,3'R)-3'-hydroxy-3'-methylbenanomicin A in the form of the free acid were obtained from 100 mg of nona-O-acetyl-desalaninebenanomicin A and 168 mg of para-toluenesulfonate of D-allothreonine diphenylmethyl ester. FABMS: 857(M⁻).

EXAMPLE 8

Preparation of (2'R)-3'-methylbenanomicin A [the D-butyrine derivative]

In a similar manner to the preparation process as described above in Example 4, 7.7 mg of (2'R)-3'-methylbenanomicin A in the form of the free acid were obtained from 100 mg of nona-O-acetyl-desalaninebenanomicin A and 168 mg of para-toluenesulfonate of D-butyrine diphenylmethyl ester. FABMS: 841(M⁻).

EXAMPLE 9

Preparation of 2'-demethylbenanomicin A [the glycine derivative]

In acetonitrile were dissolved 100 mg of nona-O-acetyl-desalaninebenanomicin A as obtained in Example 3 and 72 mg of 1-hydroxybenzotriazole mono-hydrate. The resulting solution was added with 2 ml of a solution containing 66 mg of hydrochloride of glycine ethyl ester and 5 µl of N-methylmorpholine in acetonitrile. The resulting solution was added with 56 mg of dicylohexylcarbodiimide under ice-cooling, followed by reaction for one hour and then reaction at room temperature for 3 hours. The resulting reaction solution was added with 0.1 ml of acetic acid, followed by stirring for one our. The precipitate deposited was removed by filtration and the resultant filtrate was concentrated under reduced pressure. The residue obtained was dissolved in 20 ml of ethyl acetate, and the solution was washed successively with a 10% aqueous solution of citric acid, a saturated aqueous solution of sodium hydrogen carbonate and water and then dried over anhydrous magnesium sulfate. The solvent was distilled off from the dried solution under reduced pressure, whereby 103 mg of a mixture of the condensation products were obtained.

The condensation products so obtained were dissolved in 2 ml of methanol, followed by the addition of 2 ml of a 1M aqueous solution of sodium hydroxide. The mixture obtained was stirred overnight at 50° C. The resulting reaction solution was ice-cooled and was then adjusted to pH 2.0 with 1M hydrochloric acid. The solid precipitated was separated by centrifugation, whereby a red solid was obtained. This solid was purified by chromatography on a silica gel column (with developing solvent made of chloroform-butanol-pyridine-water, 4:2:2.5:0.3), whereby the pyridine salt of 2'-demethylbenanomicin A was afforded. The pyridine salt was dissolved in 300 ml of water, followed by adjusting to pH 2.0 with 1M hydrochloric acid. The precipitate deposited was separated by centrifugation, whereby 46 mg of 2'-demethylbenanomicin A in the form of the free acid were obtained.

EXAMPLE 10

Preparation of 3'-hydroxybenanomicin A [the D-serine derivative]

In a similar manner to the preparation process as described above in Example 9, 21 mg of 3'-hydroxybenanomicin A in the form of the free acid were yielded from 100 mg of the nona-O-acetyl-desalaninebenanomicin A as obtained in Example 3 and 100 mg of D-serine benzyl ester hydrochloride.

EXAMPLE 11

Preparation of 2'-carboxy-2'-demethylbenanomicin A [the aminomalonic acid derivative]

In a similar manner to the preparation process as described above in Example 9, 51 mg of the disodium salt of 2'-carboxy-2'-demethylbenanomicin A were afforded from 100 mg of the nona-O-acetyl-desalaninebenanomicin A as obtained in Example 3 and 77 mg of aminomalonic acid diethyl ester. FABMS: 901(M$^-$).

EXAMPLE 12

Preparation of benanomicin A

In a similar manner to the preparation process as described above in Example 9, 41 mg of benanomicin A in the form of the free acid were produced from 100 mg of the nona-O-acetyl derivative as obtained in Example 3 and 129 mg of para-toluenesulfonate of D-alanine benzyl ester.

Industrial Utilizability of Invention

The desalaninebenanomicin A derivative as obtained according to the present invention and having the general formula (I) is a novel semi-synthetic antibiotic having antifungal activities and a low toxicity, and hence it is useful as an antifungal drug for therapeutic treatment of fungal infections. Desalaninebenanomicin A may be linked to a variety of amino acids to produce amino acid derivatives of desalaninebenanomicin A, and it is also useful as an intermediate for the synthesis of such amino acid derivatives of desalaninebenanomicin A.

We claim:

1. A process for the preparation of an antifungal desalaninebenanomicin A derivative having the formula (I):

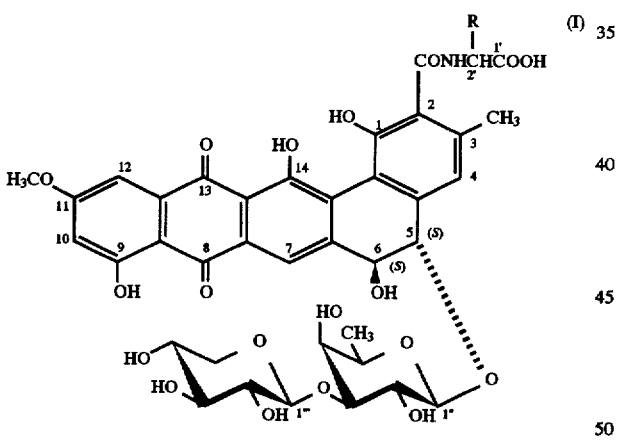

where R is selected from the group consisting of a $C_{2-5}$ alkyl group, a $C_{2-5}$ hydroxyalkyl group, a carboxyl group and a lower alkoxycarbonyl group, which process comprises consecutive steps of:

(a) protecting the terminal carboxyl group of the side chain at the 2-position of benanomicin A with an ester-forming group selected from the group consisting of a lower alkyl group, a diphenyl-methyl group and a methoxybenzyl group, (b) protecting each of the nine hydroxyl groups of the resulting benanomicin A ester with a hydroxy-protecting group, (c) subjecting the resultant nona-O-protected benanomicin A ester to a reaction for iminoetherification using a Meerwein reagent, a trialkyloxonium tetrafluoroborate, so that the amido-linkage of benanomicin A is changed into iminoether, to provide a protected iminoether derivative of benanomicin A having the formula (B):

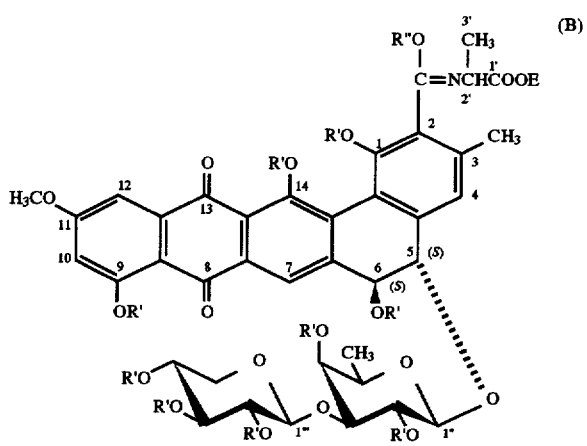

where E represents the ester-forming group, R' represents the hydroxyl-protecting group and R" represents a lower alkyl group coming from the Meerwein reagent employed, (d) removing both the hydroxyl-protecting groups and the carboxyl-protecting group from the compound of the above formula (B) to produce an iminoether compound having the formula (C):

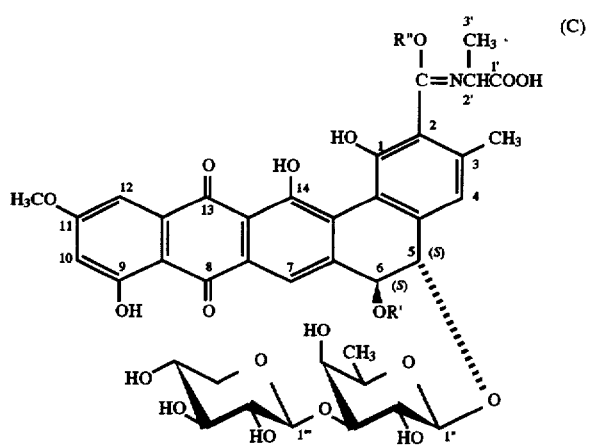

where R" has the same meaning as defined above, (e) cleaving the iminoether-bond of the compound (C) by heating the compound (C) in a mixed solution of acetone and water under reflux to give a methyl ester of the desalaninebenanomicin A having the formula (II):

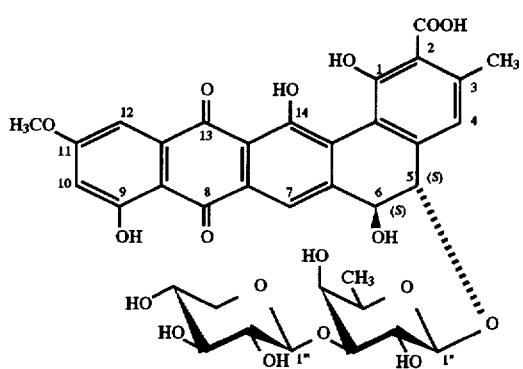

(f) treating said methyl ester of desalaninebenanomicin A of the formula (II) by alkaline hydrolysis and then with acid to give desalaninebenanomicin A of the formula (II) in the form of free acid, (g) protecting the nine hydroxyl groups of desalanine benanomicin A of the formula (II) each with a hydroxyl-protecting group chosen from a lower alkanoyl group and an aroyl group, (h) condensing the resultant nona-O-protected derivative with an amino acid ester of the formula (III'):

where R is selected from the group consisting of a $C_{2-5}$ alkyl group, $C_{2-5}$ hydroxyalkyl group, carboxyl group or a lower alkoxycarbonyl group and R' represents a lower alkyl group, to produce such a nona-O-protected desalaninebenanomicin A derivative having the formula (T):

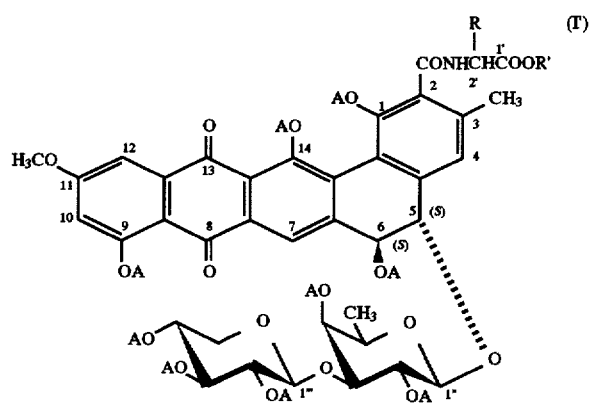

wherein R and R' are as defined above and A denotes the hydroxyl-protecting group which is a lower alkanoyl group or an aroyl group, and (i) removing the hydroxyl-protecting groups (A) as well as the carboxyl-protecting group (R') from the resulting condensation product of the formula (T) above.

2. A process as claimed in claim 1 wherein the amino acid ester of the formula (III') is selected from the group consisting of L-threonine diphenylmethyl ester; D-threonine diphenylmethyl ester; D-allothreonine diphenylmethyl ester; and D-butyrine diphenylmethyl ester.

3. A process for the preparation of desalaninebenanomicin A having the formula (II):

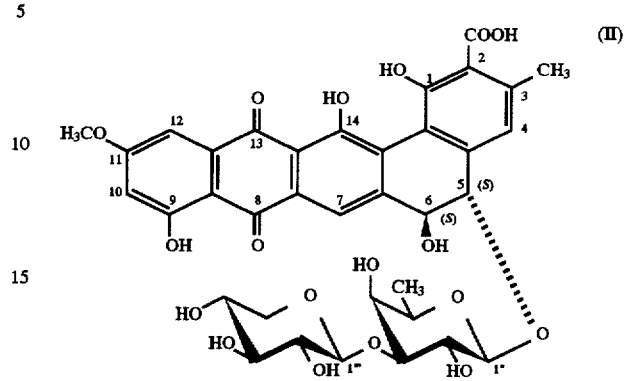

which process comprises the consecutive steps of:

(i) protecting the terminal carboxyl group of the side chain at the 2-position of benanomicin A with an ester-forming group selected from the group consisting of a lower alkyl group, a diphenylmethyl group and a methoxybenzyl group, (ii) protecting each of the nine hydroxyl groups of the resulting benanomicin A ester with a hydroxyl-protecting group, (iii) subjecting the resultant nona-O-protected benanomicin A ester to a reaction for iminoetherification using a Meerwein reagent, a trialkyloxonium tetrafluoroborate, so that the amido-linkage of benanomicin A is changed into iminoether, to provide a protected iminoether derivative of benanomicin A having the formula (B):

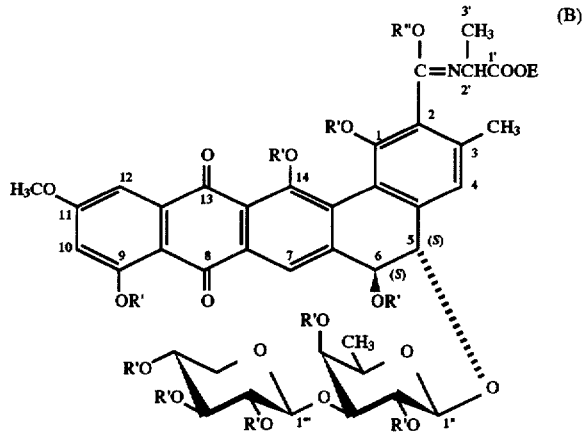

where E represents the ester-forming group, R' represents the hydroxyl-protecting group and R" represents a lower alkyl group coming from the Meerwein reagent employed, (iv) removing both the hydroxyl-protecting groups and carboxyl-protecting group from the compound of the above formula (B), to produce an iminoether compound having the formula (C):

(C)

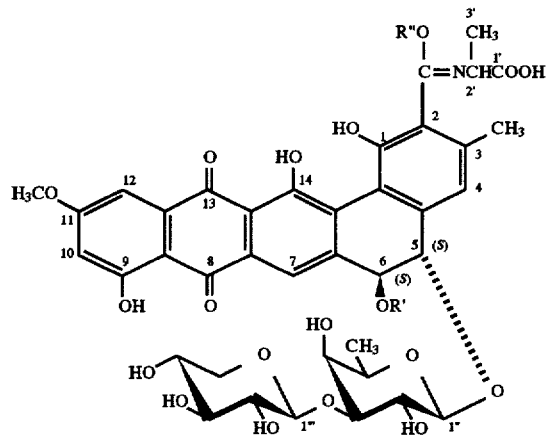

where R" has the same meaning as defined above, (v) cleaving the iminoether-bond of the compound (C) by heating the compound (C) in a mixed solution of acetone and water under refluxing, to give methyl ester of the desalanine-benanomicin A having the formula (II):

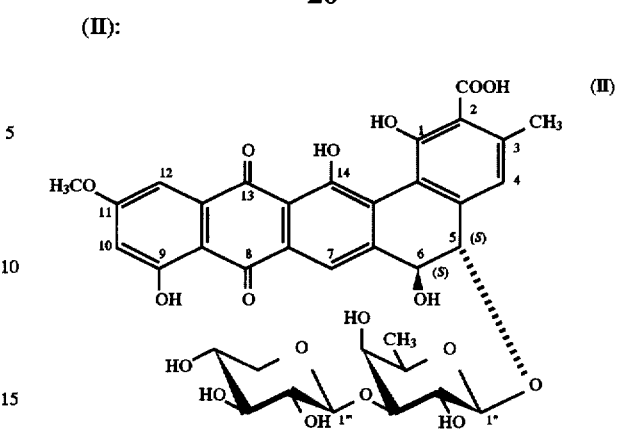

(vi) and treating said methyl ester of desalaninebenanomicin A of the formula (II) by alkaline hydrolysis and then with acid to give desalaninebenanomicin A of the formula (II) in the form of free acid.

* * * * *